United States Patent
Yin et al.

(10) Patent No.: US 11,463,643 B2
(45) Date of Patent: Oct. 4, 2022

(54) IMAGE SENSING DEVICE AND IMAGE SENSING METHOD

(71) Applicant: Guangzhou Tyrafos Semiconductor Technologies Co., LTD, Guangzhou (CN)

(72) Inventors: Ping-Hung Yin, Taipei (TW); Jia-Shyang Wang, Miaoli County (TW)

(73) Assignee: Guangzhou Tyrafos Semiconductor Technologies Co., LTD, Guangzhou (CN)

(*) Notice: Subject to any disclaimer, the term of this patent is extended or adjusted under 35 U.S.C. 154(b) by 0 days.

(21) Appl. No.: 17/403,885

(22) Filed: Aug. 17, 2021

(65) Prior Publication Data
US 2022/0103767 A1 Mar. 31, 2022

Related U.S. Application Data

(60) Provisional application No. 63/084,010, filed on Sep. 28, 2020.

(51) Int. Cl.
| | |
|---|---|
| *H04N 5/369* | (2011.01) |
| *H04N 5/33* | (2006.01) |
| *H04N 5/3745* | (2011.01) |
| *H04N 5/343* | (2011.01) |
| *H04N 5/353* | (2011.01) |
| *H04N 5/378* | (2011.01) |
| *A61B 1/05* | (2006.01) |

(52) U.S. Cl.
CPC ......... *H04N 5/36965* (2018.08); *H04N 5/343* (2013.01); *H04N 5/353* (2013.01); *H04N 5/378* (2013.01); *A61B 1/05* (2013.01); *H04N 5/332* (2013.01)

(58) Field of Classification Search
None
See application file for complete search history.

(56) References Cited

U.S. PATENT DOCUMENTS

| | | | |
|---|---|---|---|
| 9,036,065 B1 | 5/2015 | Vogelsang | |
| 2018/0376090 A1* | 12/2018 | Liu | H04N 5/378 |

FOREIGN PATENT DOCUMENTS

| | | |
|---|---|---|
| TW | I501641 | 9/2015 |

OTHER PUBLICATIONS

"Office Action of Taiwan Counterpart Application", dated Feb. 11, 2022, p. 1-p. 6.

* cited by examiner

*Primary Examiner* — Mark T Monk
(74) *Attorney, Agent, or Firm* — JCIPRNET

(57) ABSTRACT

An image sensing device and an image sensing method are provided. The image sensing device includes a pixel array and a readout circuit. The pixel array includes multiple sensing sub-pixels arranged in an array. During a first exposure period of a frame period, the sensing sub-pixels are simultaneously exposed to respectively store multiple first sensing signals in multiple storage units of the sensing sub-pixels. During multiple first readout periods of the frame period, the readout circuit sequentially reads out the first sensing signals stored in the storage units during different periods. During each of multiple dynamic sensing periods of the frame period, all or part of the sensing sub-pixels are reset and then simultaneously exposed again, and the readout circuit then simultaneously reads out multiple second sensing signals of the sensing sub-pixels.

22 Claims, 8 Drawing Sheets

IMAGE SENSING DEVICE AND IMAGE SENSING METHOD

CROSS-REFERENCE TO RELATED APPLICATION

This application claims the priority benefit of U.S. Provisional Application No. 63/084,010, filed on Sep. 28, 2020. The entirety of the above-mentioned patent application is hereby incorporated by reference herein and made a part of this specification.

BACKGROUND

Technical Field

The disclosure relates to a sensing technology, and more particularly to an image sensing device and an image sensing method.

Description of Related Art

If the current image sensor needs to implement image sensing and dynamic visual sensing, the image sensor will use part of the sensing sub-pixels for image sensing and use the other part of the sensing sub-pixels for dynamic visual sensing. In other words, if the traditional image sensor needs to implement the image sensing function and the dynamic visual sensing function, the image resolution will be reduced, and the image sensor needs additional circuit configuration cost (such as having more readout circuit requirements). In view of this, regarding how to implement an image sensor that can simultaneously have the image sensing function and the dynamic visual sensing function, and can provide an image sensing result with higher image resolution, several embodiments will be provided below.

SUMMARY

The disclosure provides an image sensing device and an image sensing method, which can implement good image sensing and dynamic visual sensing functions.

The image sensing device of the disclosure includes a pixel array and a readout circuit. The pixel array includes multiple sensing sub-pixels arranged in an array. The readout circuit is coupled to the pixel array. During a first exposure period of a frame period, the sensing sub-pixels are simultaneously exposed to respectively store multiple first sensing signals in multiple storage units of the sensing sub-pixels. During multiple first readout periods of the frame period, the readout circuit sequentially reads out the first sensing signals stored in the storage units during different periods. During each of multiple dynamic visual sensing periods of the frame period, all or part of the sensing sub-pixels are reset and then simultaneously exposed again, and the readout circuit then simultaneously reads out multiple second sensing signals of the sensing sub-pixels.

The image sensing method of the disclosure is suitable for an image sensing device. The image sensing device includes a pixel array and a readout circuit. The pixel array includes multiple sensing sub-pixels arranged in an array. The image sensing method includes the following steps. During a first exposure period of a frame period, the sensing sub-pixels are simultaneously exposed to respectively store multiple first sensing signals in multiple storage units of the sensing sub-pixels. During multiple first readout periods of the frame period, the first sensing signals stored in the storage units are sequentially read out during different periods by the readout circuit. During each of multiple dynamic visual sensing periods of the frame period, all or part of the sensing sub-pixels are reset and then simultaneously exposed again, and multiple second sensing signals of the sensing sub-pixels are then simultaneously read out by the readout circuit.

Based on the above, the image sensing device and the image sensing method of the disclosure can perform image sensing and dynamic visual sensing during one frame period, and can have good image resolution.

In order for the features and advantages of the disclosure to be more comprehensible, the following specific embodiments are described in detail in conjunction with the accompanying drawings.

DETAILED DESCRIPTION OF DISCLOSED EMBODIMENTS

Figure 1:
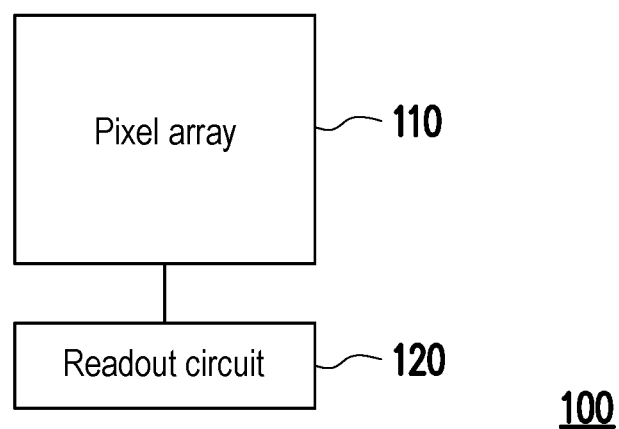
FIG. 1 is a schematic diagram of an image sensing device according to an embodiment of the disclosure.

In order for the content of the disclosure to be more comprehensible, the following embodiments are specifically cited as examples on which the disclosure can be implemented. In addition, wherever possible, elements/components/steps with the same reference numerals in the drawings and embodiments represent the same or similar parts.

Figure 2:
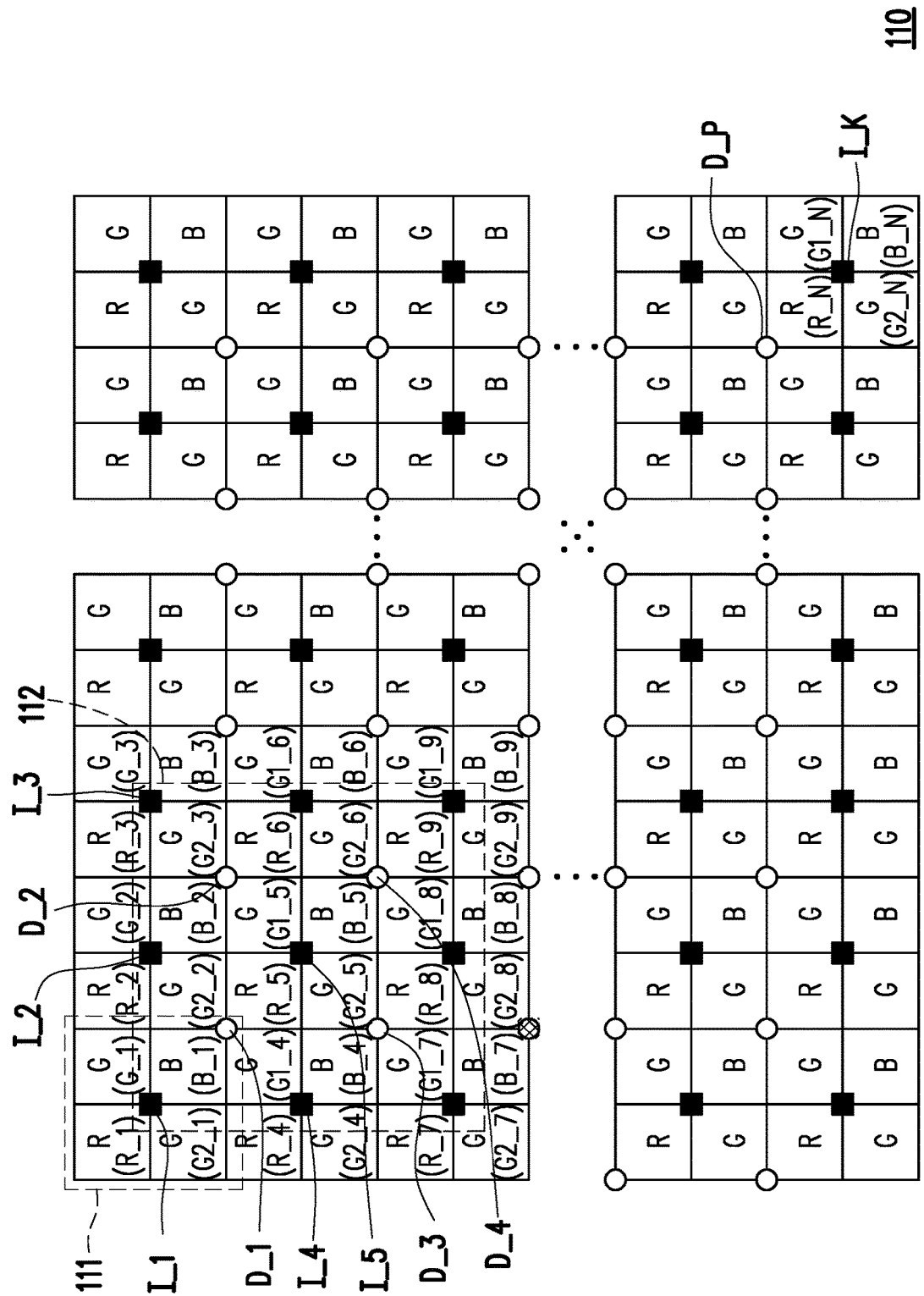
FIG. 2 is a schematic diagram of a sensing array according to an embodiment of the disclosure.

FIG. 1 is a schematic diagram of an image sensing device according to an embodiment of the disclosure. FIG. 2 is a schematic diagram of a sensing array according to an embodiment of the disclosure. Referring to FIG. 1, an image sensor device 100 includes a pixel array 110 and a readout circuit 120. The pixel array 110 is coupled to the readout circuit 120. The pixel array 110 includes multiple sensing sub-pixels R_1 to R_N, G1_1 to G1_N, G2_1 to G2_N, and B_1 to B_N, multiple readout nodes I_1 to I_K, and multiple readout nodes D_1 to D_P arranged in an array, where N, K, and P are positive integers. The readout nodes I_1 to I_K and the readout nodes D_1 to D_P are respectively configured to read out sensing results of four nearest surrounding sensing sub-pixels.

In the embodiment, the sensing sub-pixels R_1 to R_N may be red sensing sub-pixels and are configured to sense red light. The sensing sub-pixels G1_1 to G1_N may be first green sensing sub-pixels and are configured to sense green light. The sensing sub-pixels G2_1 to G2_N may be second green sensing sub-pixels and are configured to sense green light. The sensing sub-pixels B_1 to B_N may be blue sensing sub-pixels and are configured to sense blue light. In addition, in other embodiments of the disclosure, the sensing sub-pixels G2_1 to G2_N may be used as infrared light sensing sub-pixels and configured for distance sensing.

In the embodiment, one red sensing sub-pixel (such as the sensing sub-pixel R_1), one first green sensing sub-pixel (such as the sensing sub-pixel G1_1), one second green sensing sub-pixel (such as the sensing sub-pixel G2_1), and one blue sensing sub-pixel (such as the sensing sub-pixel B_1) may form one image sensing pixel (such as an image sensing pixel 111).

In the embodiment, for image sensing (as an image sensor), multiple sensing signals of four sensing sub-pixels of any image sensing pixel are time-divisionally read out by the readout circuit 120 from the same readout node (such as the readout node I_1). Specifically, the sensing signals of the sensing sub-pixels R_1, G1_1, G2_1, and B_1 are time-divisionally read out by the readout circuit 120 from the readout node I_1. The sensing signals of the sensing sub-pixels R_2, G1_2, G2_2, and B_2 are time-divisionally read out by the readout circuit 120 from the readout node I_2. The sensing signals of the sensing sub-pixels R_3, G1_3, G2_3, and B_3 are time-divisionally read out by the readout circuit 120 from the readout node I_3. By analogy, the sensing signals of other sensing sub-pixels may be read out by the readout circuit 120 from the corresponding readout node in the same manner as described above.

In the embodiment, four red sensing sub-pixels (such as the sensing sub-pixels R_5, R_6, R_8, and R_9), four first green sensing sub-pixels (such as the sensing sub-pixels G1_4, G1_5, G1_7, and G1_8), four second green sensing sub-pixels (such as the sensing sub-pixels G2_2, G2_3, G2_5, G2_6), and four blue sensing sub-pixels (such as the sensing sub-pixels B_1, B_2, B_4, and B_5) may form one dynamic visual sensing pixel (such as a dynamic visual sensing pixel 112), but the disclosure is not limited thereto. In another embodiment of the disclosure, the dynamic visual sensing pixel may also be composed of one red sensing sub-pixel (such as the sensing sub-pixel R_5), one first green sensing sub-pixel (such as the sensing sub-pixel G1_4), one second green sensing sub-pixel (such as the sensing sub-pixel G2_2), and one blue sensing sub-pixel (such as the sensing sub-pixel B_1).

In the embodiment, for dynamic visual sensing (as a dynamic vision sensor, DVS), multiple sensing signals of any sixteen sensing sub-pixels may be simultaneously read out by the readout circuit 120 from four readout nodes (such as the readout nodes D_1, D_2, D_3, and D_4). Specifically, the sensing signals of the sixteen sensing sub-pixels R_5, R_6, R_8, R_9, G1_4, G1_5, G1_7, G1_8, G2_2, G2_3, G2_5, G2_6, B_1, B_2, B_4, and B_5 are simultaneously read out by the readout circuit 120 from the readout nodes D_1, D_2, D_3, and D_4. In addition, since the outermost sensing sub-pixels (such as the sensing sub-pixels R_1, G1_1, R_2, R2_1, R_42, etc.) of the pixel array 110 are not used during dynamic visual sensing, the outermost (unused) sensing sub-pixels of the pixel array 110 may be disabled when the pixel array 110 performs dynamic visual sensing.

In the embodiment, during a first exposure period of a frame period, the sensing sub-pixels R_1 to R_N, G1_1 to G1_N, G2_1 to G2_N, and B_1 to B_N are simultaneously exposed to respectively store multiple first sensing signals in a storage unit of each sensing sub-pixel. During multiple first readout periods of the frame period, the readout circuit 120 sequentially reads out the first sensing signals stored in the storage units during different periods. During each of multiple dynamic visual sensing periods of the frame period, all or part of the sensing sub-pixels R_1 to R_N, G1_1 to G1_N, G2_1 to G2_N, and B_1 to B_N are reset and then simultaneously exposed again, and the readout circuit 120 then simultaneously reads out multiple second sensing signals of the sensing sub-pixels in the dynamic visual sensing pixel. In other words, the image sensing device 100 of the embodiment adopts a global shutter (GS) exposure operation in an image sensing mode and adopts a rolling readout operation. The image sensing device 100 of the embodiment adopts the global shutter exposure operation in a dynamic visual sensing mode.

Figure 3:
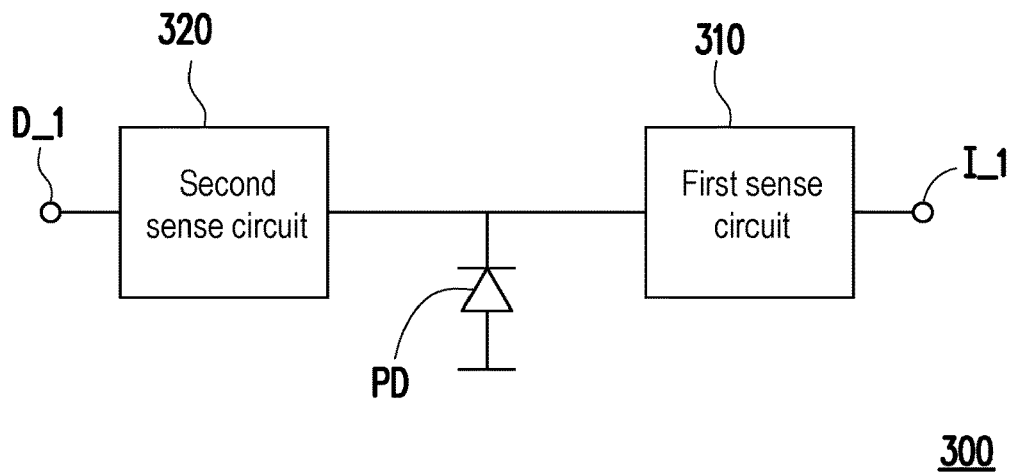
FIG. 3 is a schematic diagram of a sensing sub-pixel according to an embodiment of the disclosure.

FIG. 3 is a schematic diagram of a sensing sub-pixel according to an embodiment of the disclosure. Referring to FIG. 1, in the embodiment, the sensing sub-pixel R_1 may have the architecture of a sensing sub-pixel 300 as shown in FIG. 3, and the sensing sub-pixels R_2 to R_N, G1_2 to G1_N, G2_2 to G2_N, and B_2 to B_N also have the same architecture and may be deduced by analogy. In the embodiment, the sensing sub-pixel 300 includes a photodiode PD, a first sense circuit 310, and a second sense circuit 320. An anode of the photodiode PD is coupled to a ground voltage, and a cathode is coupled to the first sense circuit 310 and the second sense circuit 320.

In the embodiment, the first sense circuit 310 includes a storage unit. During the first exposure period, the first sense circuit 310 stores the first sensing signal provided by the photodiode PD in the storage unit. During the corresponding first readout period, the first sense circuit 310 outputs the first sensing signal stored in the storage unit from the readout node I_1. During each of the dynamic visual sensing periods, the second sense circuit 320 outputs the second sensing signal provided by the photodiode PD from the readout node D_1. Therefore, the pixel array 110 of the embodiment may use the same sensing sub-pixels to simultaneously perform image sensing and dynamic visual sensing during one frame period.

Figure 4:
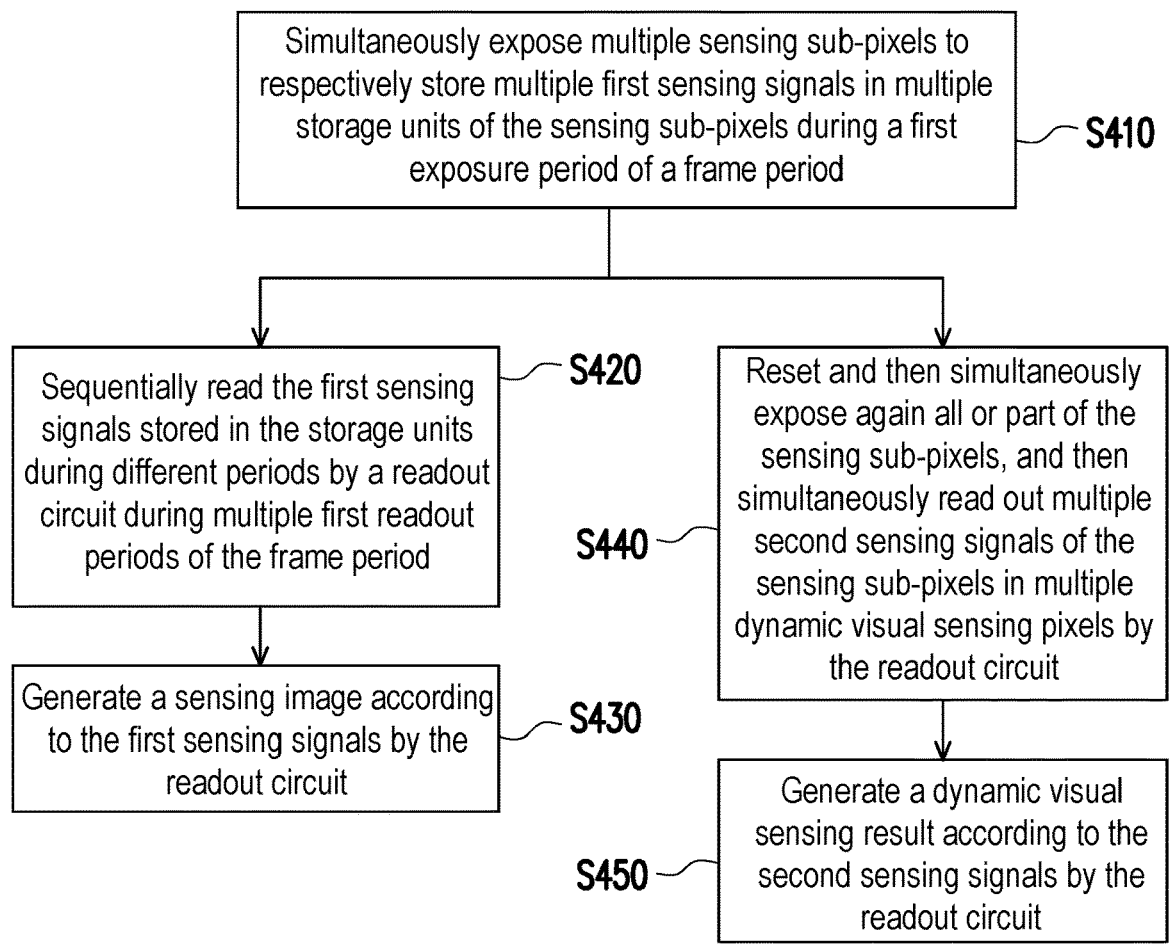
FIG. 4 is a flowchart of an image sensing method according to an embodiment of the disclosure.

FIG. 4 is a flowchart of an image sensing method according to an embodiment of the disclosure. Referring to FIG. 1, FIG. 2, and FIG. 4, the image sensing device 100 of the embodiment may execute the following Step S410 to 450 to implement an image sensing operation and a dynamic visual sensing operation during one frame period. In Step S410, during the first exposure period of the frame period, the sensing sub-pixels R_1 to R_N, G1_1 to G1_N, G2_1 to G2_N, and B_1 to B_N may be simultaneously exposed to respectively store the first sensing signals in the storage units of the sensing sub-pixels R_1 to R_N, G1_1 to G1_N, G2_1 to G2_N, and B_1 to B_N. In Step S420, during the first readout periods of the frame period, the readout circuit 120 sequentially reads the first sensing signals stored in the storage units during different periods. In Step S430, the readout circuit 120 and a back-end digital processing circuit may generate a sensing image according to the first sensing signals. In Step S440, during each of the dynamic visual sensing periods of the frame period, all or part of the sensing sub-pixels are reset and then simultaneously exposed again, and the second sensing signals of the sensing sub-pixels in the dynamic visual sensing pixels (such as the dynamic visual sensing pixel 112 of FIG. 2) are then simultaneously read out by the readout circuit 120. In Step S450, the readout circuit 120 and the back-end digital processing circuit may generate a dynamic visual sensing result according to the second sensing signals. It should be noted that Step S420 and Step S440 may be executed during the same frame period (may be simultaneous or non-simultaneous), so there is no limitation on the sequence of execution. Moreover, Step S430 and Step S450 also have no limitation on the sequence of execution. Therefore, the image sensing device 100 and the image sensing method of the embodiment can obtain the image sensing result and the dynamic visual sensing result during one frame period, and the image sensing result can have good image resolution.

Figure 5:
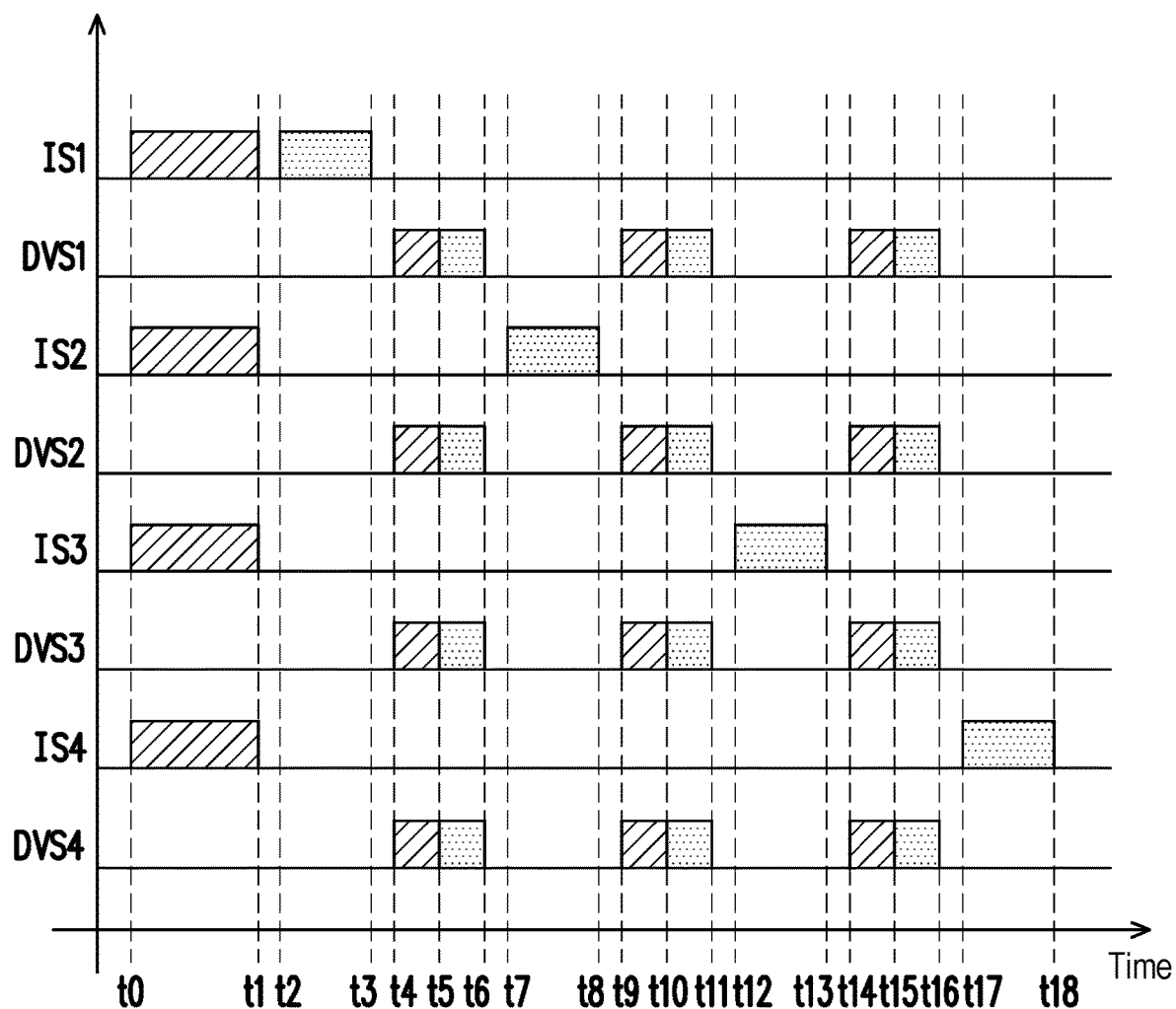
FIG. 5 is an operation time sequence diagram of multiple sensing sub-pixels during a frame period according to an embodiment of the disclosure.

FIG. 5 is an operation time sequence diagram of multiple sensing sub-pixels during a frame period according to an embodiment of the disclosure. Referring to FIG. 1, FIG. 2, and FIG. 5, the operation of the sensing sub-pixels R_5, G1_5, G2_5, and B_5 is exemplified below. Image sensing time sequences IS1 to IS4 may respectively correspond to image sensing actions of the sensing sub-pixels R_5, G1_5, G2_5, and B_5. Dynamic visual sensing time sequences DVS1 to DVS4 may respectively correspond to dynamic visual sensing actions of the sensing sub-pixels R_5, G1_5, G2_5, and B_5. From a time t0 to a time t1, the sensing sub-pixels R_5, G1_5, G2_5, and B_5 are simultaneously exposed (image sensing). From a time t2 to a time t3, the sensing signal stored in the storage unit of the sensing sub-pixel R_5 is read out from the readout node I_5. Then, from a time t4 to a time t5, the sensing sub-pixels R_5, G1_5, G2_5, and B_5 are simultaneously exposed (first dynamic visual sensing), and the sensing sub-pixels R_6, R_8, R_9, G1_4, G1_7, G1_8, G2_2, G2_3, G2_6, B_1, B_2, and B_4 are also simultaneously exposed (first dynamic visual sensing). From the time t5 to a time t6, the sensing signals of the sensing sub-pixels R_5, G1_5, G2_5, and B_5 are read out from the readout nodes D_1, D_2, D_3, and D_4, and the sensing signals of the sensing sub-pixels R_6, R_8, R_9, G1_4, G1_7, G1_8, G2_2, G2_3, G2_6, B_1, B_2, and B_4 are also simultaneously read out from the readout nodes D_1, D_2, D_3, and D_4. From a time t7 to a time t8, the sensing signal stored in the storage unit of the sensing sub-pixel G1_5 is read out from the readout node I_5. From a time t9 to a time t10, the sensing sub-pixels R_5, G1_5, G2_5, and B_5 are simultaneously exposed (second dynamic visual sensing), and the sensing sub-pixels R_6, R_8, R_9, G1_4, G1_7, G1_8, G2_2, G2_3, G2_6, B_1, B_2, and B_4 are also simultaneously exposed (second dynamic visual sensing). From the time t10 to a time t11, the sensing signals of the sensing sub-pixels R_5, G1_5, G2_5, and B_5 are read out from the readout nodes D_1, D_2, D_3, and D_4, and the sensing signals of the sensing sub-pixels R_6, R_8, R_9, G1_4, G1_7, G1_8, G2_2, G2_3, G2_6, B_1, B_2, B_4 are also simultaneously read out from the readout nodes D_1, D_2, D_3, and D_4. From a time t12 to a time t13, the sensing signal stored in the storage unit of the sensing sub-pixel G2_5 is read out from the readout node I_5. From a time t14 to a time t15, the sensing sub-pixels R_5, G1_5, G2_5, and B_5 are simultaneously exposed (third dynamic visual sensing), and the sensing sub-pixels R_6, R_8, R_9, G1_4, G1_7, G1_8, G2_2, G2_3, G2_6, B_1, B_2, and B_4 are also simultaneously exposed (third dynamic visual sensing). From the time t15 to a time t16, the sensing signals of the sensing sub-pixels R_5, G1_5, G2_5, and B_5 are read out from the readout nodes D_1, D_2, D_3, and D_4, and the sensing signals of the sensing sub-pixels R_6, R_8, R_9, G1_4, G1_7, G1_8, G2_2, G2_3, G2_6, B_1, B_2, and B_4 are also simultaneously read out from the readout nodes D_1, D_2, D_3, and D_4. From a time t17 to a time t18, the sensing signal stored in the storage unit of the sensing sub-pixel B_5 is read out from the readout node I_5.

Therefore, four image signal readout periods of the sensing sub-pixels R_5, G1_5, G2_5, and B_5 are interleaved with three dynamic visual sensing periods of the sensing sub-pixels R_5, G1_5, G2_5, and B_5, and the four image signal readout periods and the three dynamic visual sensing periods do not overlap with each other in time sequence.

In this way, the pixel array 110 of the embodiment use the same sensing sub-pixels to simultaneously perform image sensing and dynamic visual sensing during one frame period. Moreover, in the embodiment, the resolution of the sensing image generated by the pixel array 110 via the image sensing is (for example, 16 times) higher than the resolution of the sensing image generated via the dynamic visual sensing. In addition, it is worth noting that the dynamic visual sensing of the embodiment may use a back-end digital processor to compare between the three sensing images of the first to third dynamic visual sensing results, so as to judge an action result of a current sensed object through the difference or output continuous dynamic visual sensing images.

In addition, it is worth noting that since the readout operations of image sensing and dynamic visual sensing of the embodiment are performed at different time intervals, the first sense circuit of the sensing sub-pixels R_5, G1_5, G2_5, and B_5 of the embodiment and the second sense circuit of the sensing sub-pixels R_5, R_6, R_8, R_9, G1_4, G1_5, G1_7, G1_8, G2_2, G2_3, G2_5, G2_6, B_1, B_2, B_4, and B_5 of the embodiment may be coupled to the same row readout circuits or different row readout circuits of the readout circuit 120.

Figure 6:
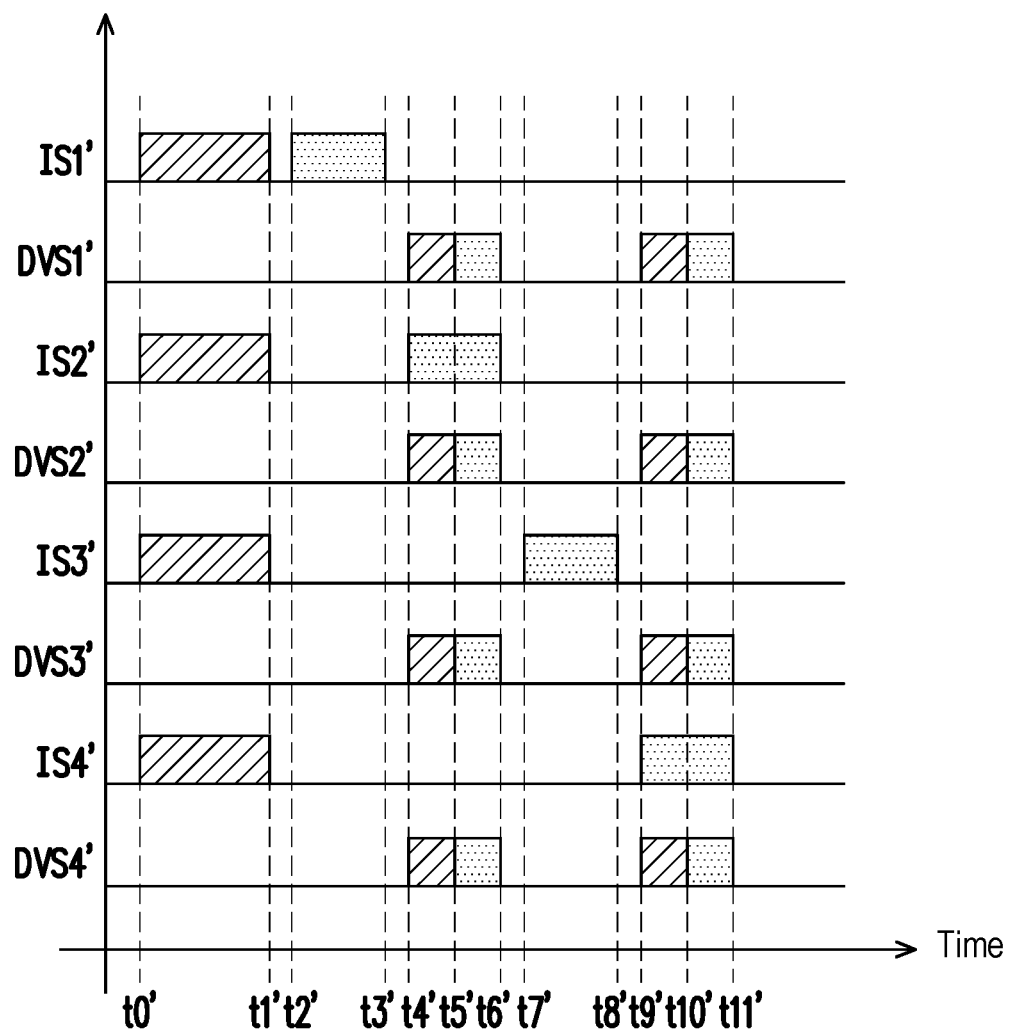
FIG. 6 is an operation time sequence diagram of multiple sensing sub-pixels during a frame period according to another embodiment of the disclosure.

FIG. 6 is an operation time sequence diagram of multiple sensing sub-pixels during a frame period according to another embodiment of the disclosure. Referring to FIG. 1, FIG. 2, and FIG. 6, the operation of the sensing sub-pixels R_5, G1_5, G2_5, and B_5 are exemplified below. Image sensing time sequences IS1' to IS4' may respectively correspond to the image sensing actions of the sensing sub-pixels R_5, G1_5, G2_5, and B_5. Dynamic visual sensing time sequences DVS1' to DVS4' may respectively correspond to the dynamic visual sensing actions of the sensing sub-pixels R_5, G1_5, G2_5, and B_5. From a time t0' to a time t1', the sensing sub-pixels R_5, G1_5, G2_5, and B_5 are simultaneously exposed (image sensing). From a time t2' to a time t3', the sensing signal stored in the storage unit of the sensing sub-pixel R_5 is read out from the readout node I_5. Then, from a time t4' to a time t5', the sensing sub-pixels R_5, G1_5, G2_5, and B_5 are simultaneously exposed (first dynamic visual sensing), and the sensing sub-pixels R_6, R_8, R_9, G1_4, G1_7, G1_8, G2_2, G2_3, G2_6, B_1, B_2, and B_4 are also simultaneously exposed (first dynamic visual sensing). From time the t5' to a time t6', the sensing signals of the sensing sub-pixels R_5, G1_5, G2_5, and B_5 are read out from the readout nodes D_1, D_2, D_3, and D_4, and the sensing signals of the sensing sub-pixels R_6, R_8, R_9, G1_4, G1_7, G1_8, G2_2, G2_3, G2_6, B_1, B_2, and B_4 are also simultaneously read out from the readout nodes D_1, D_2, D_3, and D_4. Simultaneously, from the time t4' to the time t6', the sensing signal stored in the storage unit of the sensing sub-pixel G1_1 is read out from the readout node I_5. From a time t7' to a time t8', the sensing signal stored in the storage unit of the sensing sub-pixel G2_5 is read out from the readout node I_5. From a time t9' to a time t10', the sensing sub-pixels R_5, G1_5, G2_5, and B_5 are simultaneously exposed (second dynamic visual sensing), and the sensing sub-pixels R_6, R_8, R_9, G1_4, G1_7, G1_8, G2_2, G2_3, G2_6, B_1, B_2, and B_4 are also simultaneously exposed (second dynamic visual sensing). From the time t10' to a time t11', the sensing signals of the sensing sub-pixels R_5, G1_5, G2_5, and B_5 are read out from the readout nodes D_1, D_2, D_3, and D_4, and the sensing signals of the sensing sub-pixels R_6, R_8, R_9, G1_4, G1_7, G1_8, G2_2, G2_3, G2_6, B_1, B_2, and B_4 are also simultaneously read out from the readout nodes D_1, D_2, D_3, and D_4. Simultaneously, from the time t9' to the time t11', the sensing signal stored in the storage unit of the sensing sub-pixel B_5 is read out from the readout node I_5. Therefore, an even-numbered period part (or an odd-numbered period part) of four image signal readout periods of the sensing sub-pixels R_5, G1_5, G2_5, and B_5 are interleaved with two dynamic visual sensing periods of the sensing sub-pixels R_5, G1_5, G2_5, and B_5. One of the even-numbered period part and the odd-numbered period part of the four image signal readout periods of the sensing sub-pixels R_5, G1_5, G2_5, and B_5 and the two dynamic visual sensing periods do not overlap with each other in time sequence, and the odd-numbered period part (or the even-numbered period part) of the four image signal readout periods of the sensing sub-pixels R_5, G1_5, G2_5, and B_5 and the two dynamic visual sensing periods are synchronously performed one by one.

In other words, since each sensing sub-pixel of the embodiment is designed similar to the design of the two sense circuits shown in FIG. 3, the sensing sub-pixels of the embodiment may operate an idle photodiode for dynamic visual sensing during readout periods of image sensing signals in one frame period without affecting (increasing) the time length of the frame period. Compared with the implementation time sequence of FIG. 5, the sensing result provided by the image sensing device 100 of FIG. 6 can have a higher frame rate. In addition, the dynamic visual sensing period of the disclosure is not limited to FIG. 6, and the dynamic visual sensing period (exposure+readout) may be designed to be synchronously executed during the readout period of any image sensing signal according to the design spirit thereof.

In addition, it is worth noting that since the readout operations of image sensing and dynamic visual sensing of the embodiment may be performed at the same time interval, the first sense circuit of the sensing sub-pixels R_5, G1_5, G2_5, and B_5 of the embodiment and the second sense circuit of the sensing sub-pixels R_5, R_6, R_8, R_9, G1_4, G1_5, G1_7, G1_8, G2_2, G2_3, G2_5, G2_6, B_1, B_2, B_4, and B_5 of the embodiment may be coupled to the different row readout circuits of the readout circuit 120.

Figure 7:
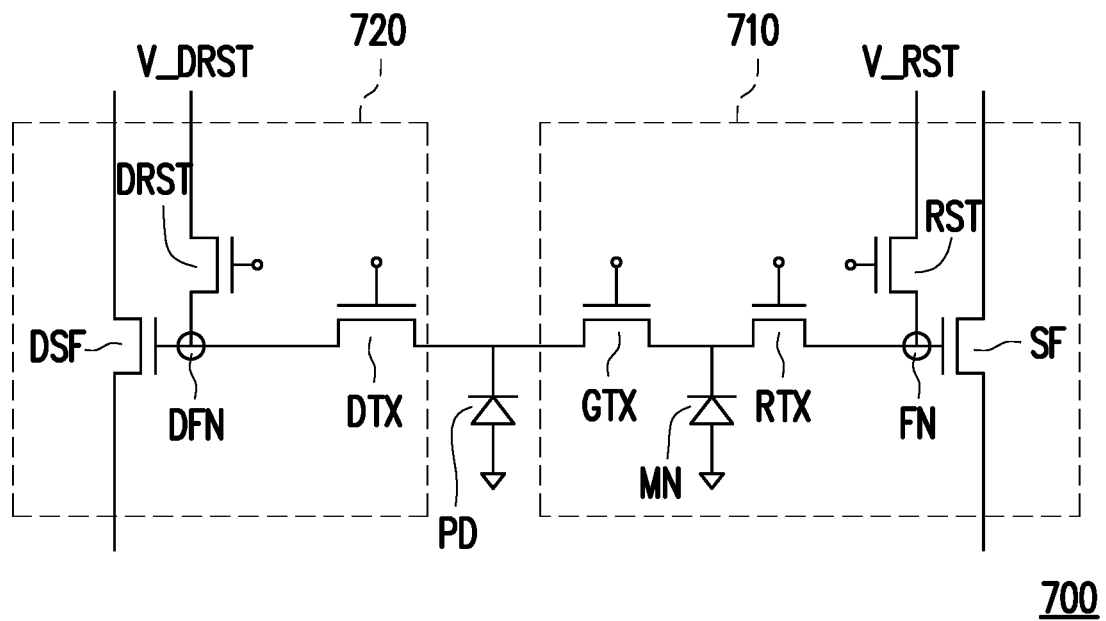
FIG. 7 is a sense circuit diagram of a sensing sub-pixel according to an embodiment of the disclosure.

FIG. 7 is a sense circuit diagram of a sensing sub-pixel according to an embodiment of the disclosure. Referring to FIG. 7, each of the sensing sub-pixels R_1 to R_N, G1_1 to G1_N, G2_1 to G2_N, and B_1 to B_N may have a circuit architecture of a sensing sub-pixel 700 as shown in FIG. 7. In the embodiment, the sensing sub-pixel 700 includes the photodiode PD, a first sense circuit 710, and a second sense circuit 720. In the embodiment, the first sense circuit 710 and the second sense circuit 720 are coupled to the photodiode PD. In the embodiment, the first sense circuit 710 includes a first transistor GTX, a storage unit MN, a second transistor RTX, a third transistor RST, and a fourth transistor SF. A first terminal of the first transistor GTX is coupled to the photodiode PD. The storage unit MN is coupled to a second terminal of the first transistor GTX. The storage unit MN may be another photodiode (not exposed to light) or an energy storage element such as a capacitor. A first terminal of the second transistor RTX is coupled to the storage unit MN. A first terminal of the third transistor RST is coupled to a reset signal V_RST. A second terminal of the third transistor RST is coupled to a second terminal of the second transistor RTX. A control terminal of the fourth transistor SF is coupled to the second terminal of the third transistor RST. In the embodiment, the control terminal of the fourth transistor SF is coupled to a readout node FN (which may be, for example, the readout node I1 in FIG. 2 and FIG. 3). The third transistor RST may reset a potential of the readout node FN and/or reset the photodiode PD. When the second transistor RTX is turned on, a second terminal of the fourth transistor SF may output a result of a sensing signal stored in the storage unit MN.

In the embodiment, the second sense circuit 720 includes a fifth transistor DTX, a sixth transistor DRST, and a seventh transistor DSF. A first terminal of the fifth transistor DTX is coupled to the photodiode PD. A first terminal of the sixth transistor DRST is coupled to another reset signal V_DRST. A second terminal of the sixth transistor DRST is coupled to a second terminal of the fifth transistor DTX. A control terminal of the seventh transistor DSF is coupled to the second terminal of the sixth transistor DRST. In the embodiment, the control terminal of the seventh transistor DSF is coupled to a readout node DFN (which may be, for example, the readout node D1 in FIG. 2 and FIG. 3). The sixth transistor DRST may reset a potential of the readout node DFN and/or reset the photodiode PD. When the fifth transistor DTX is turned on, a second terminal of the seventh transistor DSF may output a sensing signal of the photodiode PD.

Figure 8:
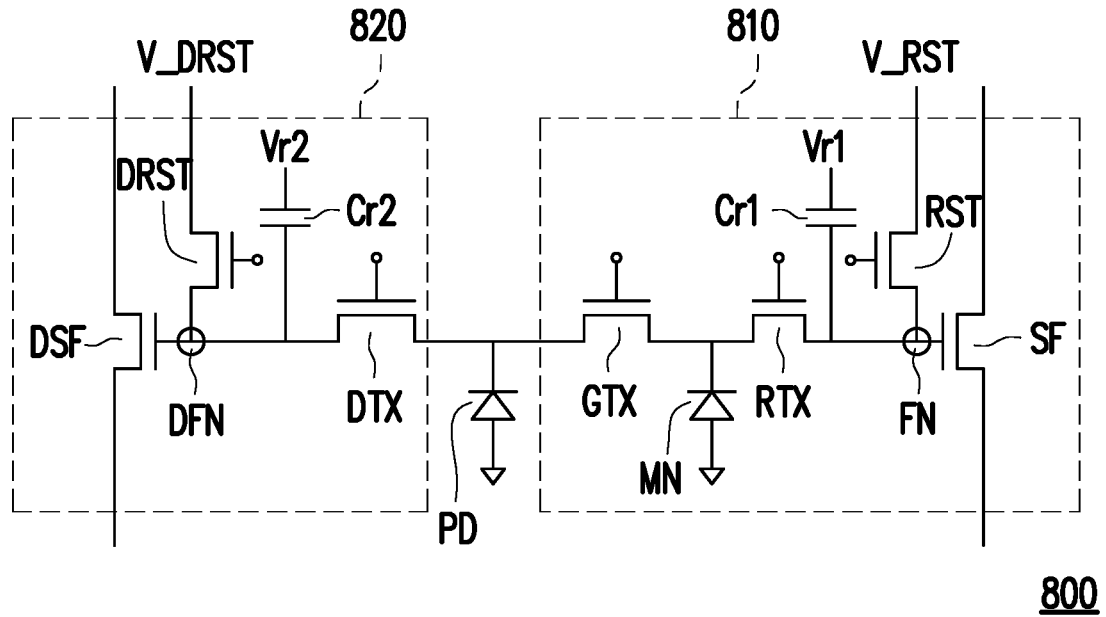
FIG. 8 is a sense circuit diagram of a sensing sub-pixel according to another embodiment of the disclosure.

FIG. 8 is a sense circuit diagram of a sensing sub-pixel according to another embodiment of the disclosure. Referring to FIG. 8, each of the sensing sub-pixels R_1 to R_N, G1_1 to G1_N, G2_1 to G2_N, and B_1 to B_N may have a circuit architecture of a sensing sub-pixel 800 as shown in FIG. 8. In the embodiment, the sensing sub-pixel 800 includes the photodiode PD, a first sense circuit 810, and a second sense circuit 820. In the embodiment, the first sense circuit 810 and the second sense circuit 820 are coupled to the photodiode PD. The internal circuit elements of the first sense circuit 810 and the second sense circuit 820 of FIG. 8 include the internal circuit elements of the first sense circuit 710 and the second sense circuit 720 of FIG. 7, so there will be no repetition. The difference from FIG. 7 is that the first sense circuit 810 of the embodiment also includes a first capacitor Cr1. A first terminal of the first capacitor Cr1 may be coupled to a ramp signal Vr1 (a sampled ramp signal). The ramp signal Vr1 may be an up ramp signal or a down ramp signal. A second terminal of the first capacitor Cr1 is coupled to the second terminal of the second transistor RTX. In the embodiment, the second sense circuit 820 also includes a second capacitor Cr2. A first terminal of the second capacitor Cr2 is coupled to another ramp signal Vr2 (a sampled ramp signal). The another ramp signal Vr2 may be another up ramp signal or another down ramp signal. A second terminal of the second capacitor Cr2 is coupled to the second terminal of the fifth transistor DTX.

In this regard, for example, the sensing sub-pixel R_1 and the sensing sub-pixel R_4 of FIG. 2 may be differentially outputted. In this regard, the two readout nodes of the first sense circuit of the sensing sub-pixel R_1 and the sensing sub-pixel R_4 may be, for example, coupled to a first input terminal and a second input terminal of an analog-to-digital converter (ADC). The two readout nodes of the second sense circuit of the sensing sub-pixel R_1 and the sensing sub-pixel R_4 may also be, for example, coupled to the first input terminal and the second input terminal of the analog-to-digital converter.

Figure 9:
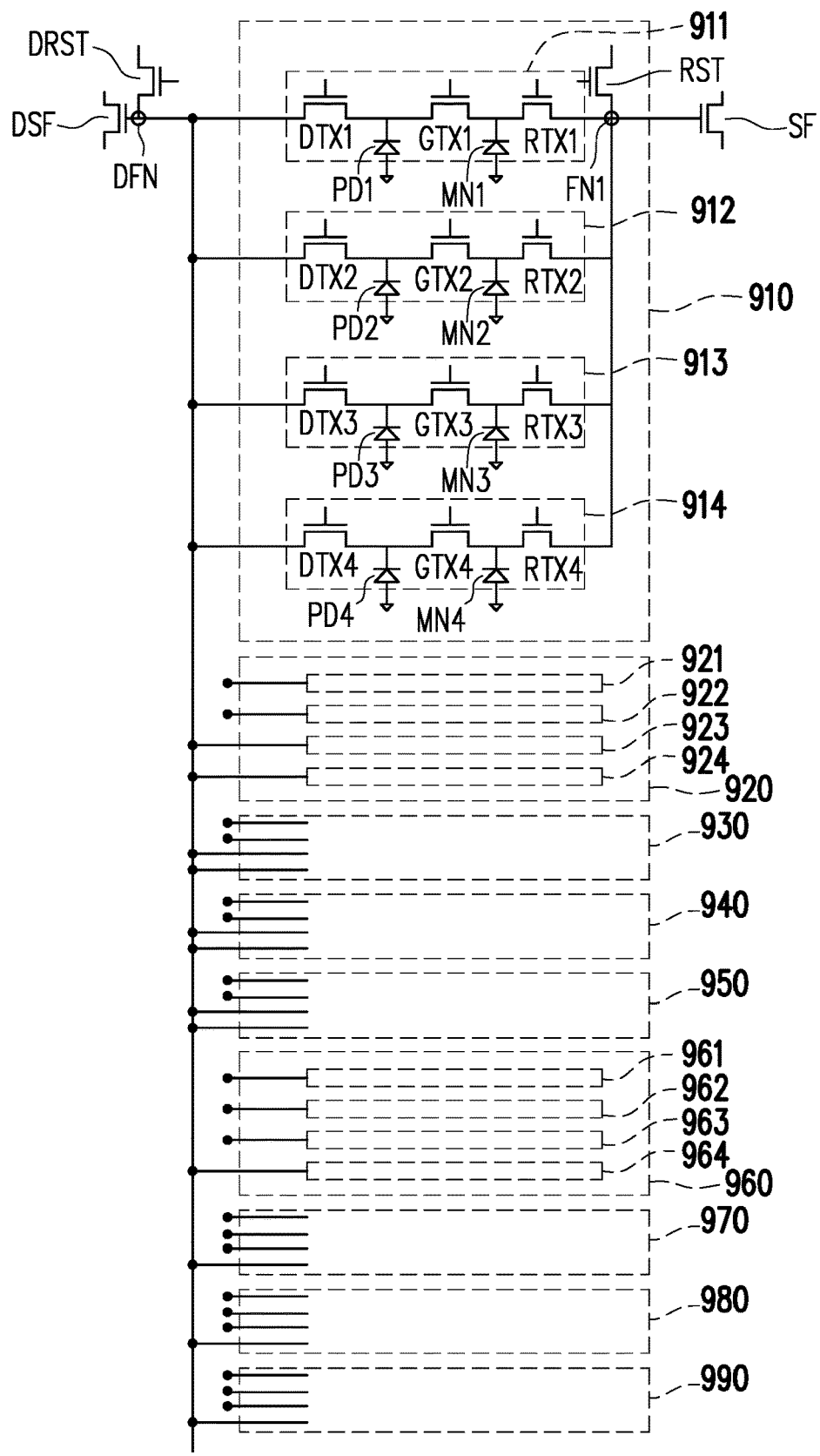
FIG. 9 is a sense circuit diagram of multiple sensing sub-pixels according to an embodiment of the disclosure.

FIG. 9 is a sense circuit diagram of multiple sensing sub-pixels according to an embodiment of the disclosure. Referring to FIG. 2 first, every four of the sensing sub-pixels R_1 to R_N, G1_1 to G1_N, G2_1 to G2_N, and B_1 to B_N in the sensing array 110 are coupled to the same fourth transistor (4-share). With reference to FIG. 9, a sensing pixel 910 may be coupled to the same third transistor RST and the same fourth transistor SF as the sensing sub-pixels R_5, G1_5, G2_5, and B_5. In the embodiment, a sense circuit 911 of the sensing sub-pixel R_5 may include a photodiode PD1, a first transistor GTX1, a storage unit MN1, and a second transistor RTX1. A sense circuit 912 of the sensing sub-pixel G1_5 may include a photodiode PD2, a first transistor GTX2, a storage unit MN2, and a second transistor RTX2. A sense circuit 913 of the sensing sub-pixel G2_5 may include a photodiode PD3, a first transistor GTX3, a storage unit MN3, and a second transistor RTX3. A sense circuit 914 of the sensing sub-pixel B_5 may include a photodiode PD4, a first transistor GTX4, a storage unit MN4, and a second transistor RTX4. In this regard, for the coupling manner of the internal circuit elements of the first sense circuit of each sensing sub-pixel in the embodiment, reference may be made to the description of the embodiment in FIG. 7, so there will be no repetition. In the embodiment, the sensing sub-pixels R_5, G1_5, G2_5, and B_5 are coupled to the same third transistor RST and the same fourth transistor SF. Therefore, the sensing pixel 910 may time-divisionally turn on the second transistors RTX1, RTX2, RTX3, and RTX4 to time-divisionally read out the sensing signals from the fourth transistor SF, so as to implement the signal readout operation of time-divisionally reading out the image sensing signals according to the embodiment of FIG. 5 or FIG. 6.

Referring to FIG. 2 and FIG. 9 simultaneously, every sixteen sensing sub-pixels in all or part of the sensing sub-pixels R_1 to R_N, G1_1 to G1_N, G2_1 to G2_N, and B_1 to B_N in the sensing array 110 are coupled to the same seventh transistor (16-share). With reference to FIG. 9, sensing pixels 910 to 990 may include the sensing sub-pixels R_5, R_6, R_8, R_9, G1_4, G1_5, G1_7, G1_8, G2_2, G2_3, G2_5, G2_6, B_1, B_2, B_4, and B_5, and the sensing sub-pixels R_5, R_6, R_8, R_9, G1_4, G1_5, G1_7, G1_8, G2_2, G2_3, G2_5, G2_6, B_1, B_2, B_4, and B_5 are coupled to the same seventh transistor. The sensing pixel 910 may include the sensing sub-pixels R_5, G1_5, G2_5, and B_5, and the sensing sub-pixels R_5, G1_5, G2_5, and B_5 are coupled to the same third transistor RST and the same fourth transistor SF. The sensing pixel 920 may include the sensing sub-pixels R_2, G1_2, G2_2, and B_2, and the sensing sub-pixels R_2, G1_2, G2_2, and B_2 are coupled to the same third transistor and the same fourth transistor. The sensing pixel 930 may include the sensing sub-pixels R_4, G1_4, G2_4, and B_4, and the sensing sub-pixels R_4, G1_4, G2_4, and B_4 are coupled to the same third transistor and the same fourth transistor. The sensing pixel 940 may include the sensing sub-pixels R_6, G1_6, G2_6, and B_6, and the sensing sub-pixels R_6, G1_6, G2_6, and B_6 are coupled to the same third transistor and the same fourth transistor. The sensing pixel 950 may include the sensing sub-pixels R_8, G1_8, G2_8, and B_8, and the sensing sub-pixels R_8, G1_8, G2_8, and B_8 are coupled to the same third transistor and the same fourth transistor. The sensing pixel 960 may include the sensing sub-pixels R_1, G1_1, G2_1, and B_1, and the sensing sub-pixels R_1, G1_1, G2_1, and B_1 are coupled to the same third transistor and the same fourth transistor. The sensing pixel 970 may include the sensing sub-pixels R_3, G1_3, G2_3, and B_3, and the sensing sub-pixels R_3, G1_3, G2_3, and B_3 are coupled to the same third transistor and the same fourth transistor. The sensing pixel 980 may include the sensing sub-pixels R_7, G1_7, G2_7, and B_7, and the sensing sub-pixels R_7, G1_7, G2_7, and B_7 are coupled to the same third transistor and the same fourth transistor. The sensing pixel 990 may include the sensing sub-pixels R_9, G1_9, G2_9, and B_9, and the sensing sub-pixels R_9, G1_9, G2_9, and B_9 are coupled to the same third transistor and the same fourth transistor.

In the embodiment, the sense circuit 911 of the sensing sub-pixel R_5 of the sensing pixel 910 may further include a fifth transistor DTX1. The sense circuit 912 of the sensing sub-pixel G1_5 of the sensing pixel 910 may further include a fifth transistor DTX2. The sense circuit 913 of the sensing sub-pixel G2_5 of the sensing pixel 910 may further include a fifth transistor DTX3. The sense circuit 914 of the sensing sub-pixel B_5 of the sensing pixel 910 may further include a fifth transistor DTX4. In this regard, for the coupling manner of the internal circuit elements of the sense circuit of each sensing sub-pixel of the embodiment, reference may be made to the description of the embodiment in FIG. 7, so there will be no repetition. In the embodiment, the sensing sub-pixels R_5, G1_5, G2_5, and B_5 are coupled to the same sixth transistor DRST and seventh transistor DSF.

In the embodiment, sense circuits 923 and 924 of the sensing sub-pixels G2_2 and B_2 of the sensing pixel 920 are also coupled to the same sixth transistor DRST and seventh transistor DSF, and sense circuits 921 and 922 of the sensing sub-pixels R_2 and G1_2 are not coupled to the sixth transistor DRST and the seventh transistor DSF or are coupled to another sixth transistor and another seventh transistor. By analogy, sense circuits of the sensing sub-pixels G1_4 and B_4 of the sensing pixel 930 are also coupled to the same sixth transistor DRST and seventh transistor DSF, and sense circuits of the sensing sub-pixels R_4 and G2_4 are not coupled to the sixth transistor DRST and the seventh transistor DSF or are coupled to another sixth transistor and another seventh transistor. Sense circuits of the sensing sub-pixels R_6 and G2_6 of the sensing pixel 940 are also coupled to the same sixth transistor DRST and seventh transistor DSF, and sense circuits of the sensing sub-pixels G1_6 and B_6 are not coupled to the sixth transistor DRST and the seventh transistor DSF or are coupled to another sixth transistor and another seventh transistor. Sense circuits of the sensing sub-pixels R_8 and G1_8 of the sensing pixel 950 are also coupled to the same sixth transistor DRST and seventh transistor DSF, and sense circuits of the sensing sub-pixels G2_8 and B_8 are not coupled to the sixth transistor DRST and the seventh transistor DSF or are coupled to another sixth transistor and another seventh transistor.

In the embodiment, a sense circuit 964 of the sensing sub-pixel B_1 of the sensing pixel 960 is also coupled to the sixth transistor DRST and the seventh transistor DSF, and sense circuits 961 to 963 of the sensing sub-pixels R_1, G1_1, and G2_1 are not coupled to the sixth transistor DRST and the seventh transistor DSF or are coupled to another sixth transistor and another seventh transistor. By analogy, a sense circuit of the sensing sub-pixel G2_3 of the sensing pixel 970 is also coupled to the sixth transistor DRST and the seventh transistor DSF, and sense circuits of the sensing sub-pixels R_3, G1_3, and B_3 are not coupled to the sixth transistor DRST and the seventh transistor DSF and are coupled to another sixth transistor and another seventh transistor. A sense circuit of the sensing sub-pixel G1_7 of the sensing pixel 980 is also coupled to the sixth transistor DRST and the seventh transistor DSF, and sense circuits of the sensing sub-pixels R_7, G2_7, and B_7 are not coupled to the sixth transistor DRST and the seventh transistor DSF or are coupled to anther sixth transistor and another seventh transistor. A sense circuit of the sensing sub-pixel R_9 of the sensing pixel 990 is also coupled to the sixth transistor DRST and the seventh transistor DSF, and sense circuits of the sensing sub-pixels G1_9, G2_9, and B_9 are not coupled to the sixth transistor DRST and the seventh transistor DSF or are coupled to another sixth transistor and another seventh transistor.

Therefore, each of the sensing sub-pixels R_5, R_6, R_8, R_9, G1_4, G1_5, G1_7, G1_8, G2_2, G2_3, G2_5, G2_6, B_1, B_2, B_4, and B_5 of the sensing pixels 910 to 990 may simultaneously turn on the fifth transistor to simultaneously read out a sum signal result of the sensing signals from the seventh transistor DSF, so as to implement the signal readout action of simultaneously reading out the dynamic visual sensing signals according to the embodiment of FIG. 5 or FIG. 6.

Figure 10:
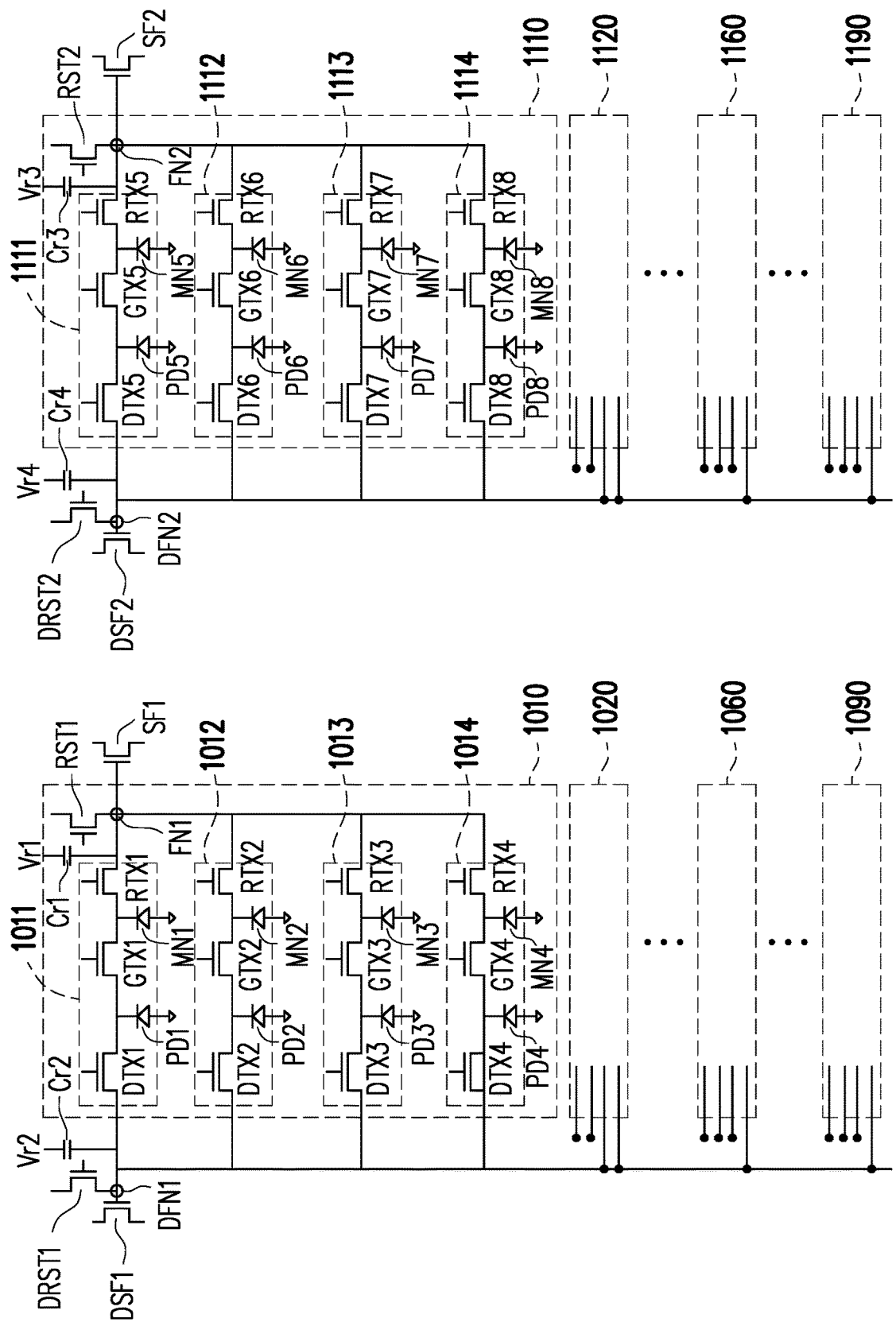
FIG. 10 is a sense circuit diagram of multiple sensing sub-pixels according to another embodiment of the disclosure.

FIG. 10 is a sense circuit diagram of multiple sensing sub-pixels according to another embodiment of the disclosure. Referring to FIG. 2 first, sixteen sensing sub-pixels of the dynamic visual sensing pixel 112 may form a differential output with sixteen other sensing sub-pixels of another sensing pixel group. With reference to FIG. 10, sensing pixels 1010 to 1090 may include the sensing sub-pixels R_5, R_6, R_8, R_9, G1_4, G1_5, G1_7, G1_8, G2_2, G2_3, G2_5, G2_6, B_1, B_2, B_4, and B_5, and for the coupling manner of the internal circuits of the sensing pixels 1010 to 1090, reference may be made to the embodiment of FIG. 9, so there will be no repetition. The sensing pixel 1010 may include the sensing sub-pixels R_5, G1_5, G2_5, and B_5. In the embodiment, a sense circuit 1011 of the sensing sub-pixel R_5 may include the first transistor GTX1, the storage unit MN1, and the second transistor RTX1. A sense circuit 1012 of the sensing sub-pixel G1_5 may include the first transistor GTX2, the storage unit MN2, and the second transistor RTX2. A sense circuit 1013 of the sensing sub-pixel G2_5 may include the first transistor GTX3, the storage unit MN3, and the second transistor RTX3. A sense circuit 1014 of the sensing sub-pixel B_5 may include the first transistor GTX4, the storage unit MN4, and the second transistor RTX4. The sense circuits 1011 to 1014 of the sensing sub-pixels R_5, G1_5, G2_5, and B_5 are coupled to the same third transistor RST1, fourth transistor SF1, and first capacitor Cr1.

In the embodiment, the sensing pixel 1110 may be another sensing pixel and may also include four sensing sub-pixels. In the embodiment, a sense circuit 1111 of another red sensing sub-pixel may include a first transistor GTX5, a storage unit MN5, and a second transistor RTX5. A sense circuit 1112 of another first green sensing sub-pixel may include a first transistor GTX6, a storage unit MN6, and a second transistor RTX6. A sense circuit 1113 of another second green sensing sub-pixel may include a first transistor GTX7, a storage unit MN7, and a second transistor RTX7. A sense circuit 1114 of another blue sensing sub-pixel may include a first transistor GTX8, a storage unit MN8, and a second transistor RTX8. The sense circuits 1111 to 1114 of the another red sensing sub-pixel, the another first green sensing sub-pixel, the another second green sensing sub-pixel, and the another blue sensing sub-pixel are coupled to the same third transistor RST2, fourth transistor SF2, and first capacitor Cr3.

In the embodiment, the first capacitor Cr1 may, for example, receive the up ramp signal Vr1, and the first capacitor Cr3 may, for example, receive a down ramp signal Vr3. Readout results of image sensing signals of the photodiode PD1 and a photodiode PD5 may be used as differential output. Readout results of image sensing signals of the photodiode PD2 and a photodiode PD6 may be used as differential output. Readout results of image sensing signals of the photodiode PD3 and a photodiode PD7 may be used as differential output. Readout results of image sensing signals of the photodiode PD4 and a photodiode PD8 may be used as differential output. Therefore, a back-end differential amplifier or the analog-to-digital converter may use the differential output results to generate the sensing image.

In the embodiment, the sensing pixel 1010 may time-divisionally turn on the second transistors RTX1, RTX2, RTX3, and RTX4, and the sensing pixel 1110 may time-divisionally turn on the second transistors RTX5, RTX6, RTX7, and RTX8. Therefore, the readout circuit may time-divisionally read out multiple differential sensing signals provided via a readout node FN1 and a readout node FN2 from the fourth transistor SF1 and the fourth transistor SF2 so as to implement the signal readout operation of time-divisionally reading out the image sensing signals according to the embodiment of FIG. 5 or FIG. 6. By analogy, the sensing pixels 1020 to 1090 and sensing pixels 1120 to 1190 may execute the same operation to time-divisionally read out the respective image sensing signals.

Referring to FIG. 2 and FIG. 10 simultaneously, every sixteen sensing sub-pixels in the sensing sub-pixels R_1 to R_N, G1_1 to G1_N, G2_1 to G2_N, and B_1 to B_N in the sensing array 110 are coupled to the same seventh transistor. In the embodiment, the sense circuit 1011 of the sensing sub-pixel R_5 may further include the fifth transistor DTX1. The sense circuit 1012 of the sensing sub-pixel G1_5 may include the fifth transistor DTX2. The sense circuit 1012 of the sensing sub-pixel G2_5 may include the fifth transistor DTX3. The sense circuit 1013 of the sensing sub-pixel B_5 may include the fifth transistor DTX4. The sense circuits 1011 to 1014 of the sensing sub-pixels R_5, G1_5, G2_5, and B_5 are coupled to the same sixth transistor DRST1, seventh transistor DSF1, and second capacitor Cr2. By analogy, the sense circuits of the sensing sub-pixels R_6, R_8, R_9, G1_4, G1_7, G1_8, G2_2, G2_3, G2_6, B_1, B_2, and B_4 in the sensing pixels 1020 to 1090 are also coupled to the sixth transistor DRST1, the seventh transistor DSF1, and the second capacitor Cr2.

In the embodiment, the sense circuit 1111 of another red sensing sub-pixel may include a fifth transistor DTX5. The sense circuit 1112 of another first green sensing sub-pixel may include a fifth transistor DTX6. The sense circuit 1113 of another second green sensing sub-pixel may include a fifth transistor DTX7. The sense circuit 1114 of another blue sensing sub-pixel may include a fifth transistor DTX8. The sense circuits 1111 to 1114 of the another red sensing sub-pixel, the another first green sensing sub-pixel, the another second green sensing sub-pixel, and the another blue sensing sub-pixel are coupled to the same sixth transistor DRST2, seventh transistor DSF2, and second capacitor Cr4. By analogy, sense circuits of twelve corresponding sensing sub-pixels in the sensing pixels 1120 to 1190 are also coupled to the sixth transistor DRST2, the seventh transistor DSF2, and the second capacitor Cr4.

In the embodiment, the second capacitor Cr2 may, for example, receive an up ramp signal, and the second capacitor Cr4 may, for example, receive a down ramp signal. Readout results of dynamic visual sensing signals of the photodiode PD1 and the photodiode PD5 may be used as differential output. Readout results of dynamic visual sensing signals of the photodiode PD2 and the photodiode PD6 may be used as differential output. Readout results of dynamic visual sensing signals of the photodiode PD3 and the photodiode PD7 may be used as differential output. Readout results of dynamic visual sensing signals of the photodiode PD4 and the photodiode PD8 may be used as differential output. Therefore, the back-end differential amplifier or the analog-to-digital converter may use the differential output results to generate the dynamic visual sensing image.

In the embodiment, the sensing pixels 1020 to 1090 may have the same circuit configuration as the sensing pixel 1010. The sensing pixels 1120 to 1190 may have the same circuit configuration as the sensing pixel 1110. Therefore, the sensing array 110 may simultaneously turn on all fifth transistors of the sensing sub-pixels R_5, R_6, R_8, R_9, G1_4, G1_5, G1_7, G1_8, G2_2, G2_3, G2_5, G2_6, B_1, B_2, B_4, and B_5, and may simultaneously turn on all fifth transistors of sixteen other sensing sub-pixels of the sensing pixels 1110 to 1190. Therefore, the readout circuit may read out the differential sensing signals provided via a readout node DFN1 and a readout node DFN2 from the seventh transistor DSF1 and the seventh transistor DSF2, so as to implement the signal readout action of the dynamic visual sensing signals according to the embodiment of FIG. 5 or FIG. 6.

In summary, the image sensing device and image sensing method of the disclosure can perform image sensing and dynamic visual sensing during one frame period. The image sensing device and the image sensing method of the disclosure can also implement the image sensing result and the dynamic visual sensing result with higher frame rate through the time sequence design of the exposure operations of image sensing and dynamic visual sensing. The image sensing device and the image sensing method of the disclosure can also implement the image sensing result and the dynamic visual sensing result with low noise and high precision through the data readout design of differential output.

Although the disclosure has been disclosed in the above embodiments, the embodiments are not intended to limit the disclosure. Persons skilled in the art may make some changes and modifications without departing from the spirit and scope of the disclosure. The protection scope of the disclosure shall be defined by the appended claims.

What is claimed is:

1. An image sensing device, comprising:
    a pixel array, comprising a plurality of sensing sub-pixels arranged in an array; and
    a readout circuit, coupled to the pixel array, wherein
    during a first exposure period of a frame period, the plurality of sensing sub-pixels are simultaneously exposed to respectively store a plurality of first sensing signals in a plurality of storage units of the plurality of sensing sub-pixels, wherein
    during a plurality of first readout periods of the frame period, the readout circuit sequentially reads out the plurality of first sensing signals stored in the plurality of storage units during different periods, wherein
    during each of a plurality of dynamic visual sensing periods of the frame period, all or part of the plurality of sensing sub-pixels are reset and then simultaneously exposed again, and the readout circuit then simultaneously reads out a plurality of second sensing signals of the plurality of sensing sub-pixels.

2. The image sensing device according to claim 1, wherein the plurality of first readout periods are interleaved with the plurality of dynamic visual sensing periods, and the plurality of first readout periods and the plurality of dynamic visual sensing periods do not overlap with each other in time sequence.

3. The image sensing device according to claim 1, wherein one of an even-numbered period part and an odd-numbered period part of the plurality of first readout periods is interleaved with the plurality of dynamic visual sensing periods, and one of the even-numbered period part and the odd-numbered period part of the plurality of first readout periods and the plurality of dynamic visual sensing periods do not overlap with each other in time sequence, wherein
    other one of the even-numbered period part and the odd-numbered period part of the plurality of first readout periods and the plurality of dynamic visual sensing periods are synchronously performed one by one.

4. The image sensing device according to claim 1, wherein the plurality of sensing sub-pixels comprise a red sensing sub-pixel, a first green sensing sub-pixel, a second green sensing sub-pixel, and a blue sensing sub-pixel.

5. The image sensing device according to claim 1, wherein the readout circuit generates a sensing image according to the plurality of first sensing signals, and the readout circuit generates a dynamic sensing result according to the plurality of second sensing signals.

6. The image sensing device according to claim 1, wherein during the plurality of first readout periods of the frame period, the readout circuit sequentially reads out another plurality of first sensing signals stored in another plurality of storage units of the plurality of sensing sub-pixels during different periods, wherein the plurality of first sensing signals and the another plurality of first sensing signals respectively form a plurality of differential signals, and the readout circuit generates a sensing image according to the plurality of differential signals.

7. The image sensing device according to claim 1, wherein during each of the plurality of dynamic visual sensing periods, the readout circuit simultaneously reads out another plurality of second sensing signals of the plurality of sensing sub-pixels, wherein the plurality of second sensing signals and the another plurality of second sensing signals respectively form another plurality of differential signals, and the readout circuit generates a dynamic visual sensing result according to the another plurality of differential signals.

8. The image sensing device according to claim 1, wherein each of the plurality of sub-pixels comprises:
    a photodiode;
    a first sense circuit, coupled to the photodiode and comprising the storage unit; and
    a second sense circuit, coupled to the photodiode, wherein
    during the first exposure period, the first sense circuit stores the first sensing signal provided by the photodiode in the storage unit, wherein
    during a corresponding first readout period, the first sense circuit outputs the first sensing signal stored in the storage unit, wherein
    during each of the plurality of dynamic visual sensing periods, the second sense circuit outputs the second sensing signal provided by the photodiode.

9. The image sensing device according to claim 8, wherein the first sense circuit and the second sense circuit are coupled to different row readout circuits of the readout circuit.

10. The image sensing device according to claim 8, wherein the first sense circuit and the second sense circuit are coupled to same row readout circuits of the readout circuit.

11. The image sensing device according to claim 8, wherein the first sense circuit comprises:
a first transistor, wherein a first terminal of the first transistor is coupled to the photodiode;
the storage unit, coupled to a second terminal of the first transistor;
a second transistor, wherein a first terminal of the second transistor is coupled to the storage unit;
a third transistor, wherein a first terminal of the third transistor is coupled to a reset signal, and a second terminal of the third transistor is coupled to a second terminal of the second transistor; and
a fourth transistor, wherein a control terminal of the fourth transistor is coupled to the second terminal of the third transistor.

12. The image sensing device according to claim 11, wherein every four sensing sub-pixels with different colors in the plurality of sensing sub-pixels are coupled to a same fourth transistor.

13. The image sensing device according to claim 11, wherein the first sense circuit further comprises:
a first capacitor, wherein a first terminal of the first capacitor is coupled to an up ramp signal or a down ramp signal, and a second terminal of the first capacitor is coupled to the second terminal of the second transistor.

14. The image sensing device according to claim 8, wherein the second sense circuit comprises:
a fifth transistor, wherein a first terminal of the fifth transistor is coupled to the photodiode;
a sixth transistor, wherein a first terminal of the sixth transistor is coupled to another reset signal, and a second terminal of the sixth transistor is coupled to a second terminal of the fifth transistor; and
a seventh transistor, wherein a control terminal of the seventh transistor is coupled to the second terminal of the sixth transistor.

15. The image sensing device according to claim 14, wherein every sixteen sensing sub-pixels in the plurality of sensing sub-pixels are coupled to a same seventh transistor.

16. The image sensing device according to claim 14, wherein the second sense circuit further comprises:
a second capacitor, wherein a first terminal of the second capacitor is coupled to another up ramp signal or another down ramp signal, and a second terminal of the second capacitor is coupled to the second terminal of the fifth transistor.

17. An image sensing method, suitable for an image sensing device, wherein the image sensing device comprises a pixel array and a readout circuit, and the pixel array comprises a plurality of sensing sub-pixels arranged in an array, the image sensing method comprising:
simultaneously exposing the plurality of sensing sub-pixels to respectively store a plurality of first sensing signals in a plurality of storage units of the plurality of sensing sub-pixels during a first exposure period of a frame period;
sequentially reading out the plurality of first sensing signals stored in the plurality of storage units during different periods by the readout circuit during a plurality of first readout periods of the frame period; and
resetting and then simultaneously exposing again all or part of the plurality of sensing sub-pixels, and then simultaneously reading out a plurality of second sensing signals of the plurality of sensing sub-pixels by the readout circuit during each of a plurality of dynamic visual sensing periods of the frame period.

18. The image sensing method according to claim 17, wherein the plurality of first readout periods are interleaved with the plurality of dynamic visual sensing periods, and the plurality of first readout periods and the plurality of dynamic visual sensing periods do not overlap with each other in time sequence.

19. The image sensing method according to claim 17, wherein one of an even-numbered period part and an odd-numbered period part of the plurality of first readout periods is interleaved with the plurality of dynamic visual sensing periods, and one of the even-numbered period part and the odd-numbered period part of the plurality of first readout periods and the plurality of dynamic visual sensing periods do not overlap with each other in time sequence, wherein
other one of the even-numbered period part and the odd-numbered period part of the plurality of first readout periods and the plurality of dynamic visual sensing periods are synchronously performed one by one.

20. The image sensing method according to claim 17, further comprising:
generating a sensing image according to the plurality of first sensing signals by the readout circuit; and
generating a dynamic visual sensing result according to the plurality of second sensing signals by the readout circuit.

21. The image sensing method according to claim 17, further comprising:
sequentially reading out another plurality of first sensing signals stored in another plurality of storage units of the plurality of sensing sub-pixels during different periods by the readout circuit during the plurality of first readout periods of the frame period, wherein the plurality of first sensing signals and the another plurality of first sensing signals respectively form a plurality of differential signals; and
generating a sensing image according to the plurality of differential signals by the readout circuit.

22. The image sensing method according to claim 17, further comprising:
simultaneously reading out another plurality of second sensing signals of the plurality of sensing sub-pixels by the readout circuit during each of the plurality of dynamic visual sensing periods, wherein the plurality of second sensing signals and the another plurality of second sensing signals respectively form another plurality of differential signals; and
generating a dynamic visual sensing result according to the another plurality of differential signals by the readout circuit.

* * * * *